(12) United States Patent
Shimomura

(10) Patent No.: US 12,336,692 B2
(45) Date of Patent: Jun. 24, 2025

(54) ENDOSCOPE SYSTEM, CONTROL METHOD, AND CONTROL PROGRAM FOR EMITTING DIFFERENT ILLUMINATION LIGHTS IN DIFFERENT PERIODS

(71) Applicant: FUJIFILM Corporation, Tokyo (JP)

(72) Inventor: Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 542 days.

(21) Appl. No.: 17/734,152

(22) Filed: May 2, 2022

(65) Prior Publication Data

US 2022/0257097 A1 Aug. 18, 2022

Related U.S. Application Data

(63) Continuation of application No. PCT/JP2020/038585, filed on Oct. 13, 2020.

(30) Foreign Application Priority Data

Dec. 10, 2019 (JP) .................................. 2019-223276

(51) Int. Cl.
  *A61B 1/06* (2006.01)
  *A61B 1/00* (2006.01)
  (Continued)

(52) U.S. Cl.
  CPC ........ *A61B 1/0655* (2022.02); *A61B 1/00165* (2013.01); *A61B 1/05* (2013.01); *G06T 7/0012* (2013.01); *G06T 7/11* (2017.01)

(58) Field of Classification Search
  CPC ..... A61B 1/00165; A61B 1/05; A61B 1/0655; A61B 1/043; A61B 1/045; A61B 1/00009; A61B 1/000095; G06T 7/11; G06T 7/0012
  See application file for complete search history.

(56) References Cited

U.S. PATENT DOCUMENTS

2002/0018649 A1   2/2002  Hakamata
2008/0009669 A1 * 1/2008  Ozawa ............... A61B 1/00045
                                                                600/101
(Continued)

FOREIGN PATENT DOCUMENTS

CN    103732119 A    4/2014
CN    106659362 A    5/2017
(Continued)

OTHER PUBLICATIONS

International Search Report issued in PCT/JP2020/038585; mailed Dec. 1, 2020.
(Continued)

*Primary Examiner* — John P Leubecker
(74) *Attorney, Agent, or Firm* — Studebaker Brackett PLLC

(57) ABSTRACT

An imaging element (23) performs imaging at a frame rate higher than a frame rate of display of a captured image displayed by a display device (7). A light source device (5) repeatedly performs an operation of continuously emitting illumination light in a first period over a plurality of consecutive frames in imaging by the imaging element (23), and then emitting illumination light having a spectrum different from a spectrum of the illumination light emitted in the first period in a second period which is a period over at least one frame in imaging by the imaging element (23).

18 Claims, 8 Drawing Sheets

(51) Int. Cl.
*A61B 1/05* (2006.01)
*G06T 7/00* (2017.01)
*G06T 7/11* (2017.01)

(56) References Cited

U.S. PATENT DOCUMENTS

| | | | |
|---|---|---|---|
| 2011/0074943 A1* | 3/2011 | Modell | H04N 25/531 |
| | | | 348/E7.085 |
| 2013/0300849 A1 | 11/2013 | Ono | |
| 2016/0330415 A1 | 11/2016 | Mizuno et al. | |
| 2016/0353972 A1 | 12/2016 | Yano et al. | |
| 2017/0112356 A1* | 4/2017 | Mitsui | H04N 23/80 |
| 2018/0067296 A1* | 3/2018 | Sugie | H04N 23/6811 |
| 2018/0267291 A1* | 9/2018 | Mikami | A61B 1/00188 |
| 2020/0022570 A1* | 1/2020 | Kennedy | A61B 1/0655 |
| 2021/0100439 A1* | 4/2021 | Hirota | A61B 1/0005 |
| 2021/0105395 A1* | 4/2021 | Tsutsui | H04N 23/71 |
| 2022/0256183 A1* | 8/2022 | Mangan | H04N 19/597 |

FOREIGN PATENT DOCUMENTS

| | | |
|---|---|---|
| JP | 2002-058631 A | 2/2002 |
| JP | 2004-321244 A | 11/2004 |
| JP | 2010-172673 A | 8/2010 |
| JP | 2011-206336 A | 10/2011 |
| JP | 2014-183909 A | 10/2014 |
| JP | 2016-019569 A | 2/2016 |
| JP | 2016-097240 A | 5/2016 |
| WO | 2015/136963 A1 | 9/2015 |
| WO | 2015/190443 A1 | 12/2015 |
| WO | 2019/221306 A1 | 11/2019 |

OTHER PUBLICATIONS

International Preliminary Report on Patentability and Written Opinion issued in PCT/JP2020/038585; issued May 17, 2022.
An Office Action; mailed by the China National Intellectual Property Administration of the People's Republic of China on Mar. 24, 2025, which corresponds to Chinese Patent Application No. 202080080787.0 and is related to U.S. Appl. No. 17/734,152.

* cited by examiner

ENDOSCOPE SYSTEM, CONTROL METHOD, AND CONTROL PROGRAM FOR EMITTING DIFFERENT ILLUMINATION LIGHTS IN DIFFERENT PERIODS

CROSS-REFERENCE TO RELATED APPLICATIONS

This application is a Continuation of PCT International Application No. PCT/JP2020/038585 filed on Oct. 13, 2020, which claims priority under 35 U.S.C § 119(a) to Japanese Patent Application No. 2019-223276 filed on Dec. 10, 2019. Each of the above application(s) is hereby expressly incorporated by reference, in its entirety, into the present application.

BACKGROUND OF THE INVENTION

1. Field of the Invention

The present invention relates to an endoscope system, a control method, and a non-transitory computer readable recording medium storing a control program.

2. Description of the Related Art

In the related art, an endoscope system is known in which continuous imaging is performed while irradiating a subject with normal light, such as white light, to display a live image. There is known an endoscope system that performs continuous imaging while irradiating a subject with special light, such as narrow band light, and performs analysis such as image-enhanced endoscopy (IEE).

In addition, as illumination light in a case of imaging, an endoscope system capable of switching between normal light and special light is known. For example, WO2015/136963A discloses an endoscope system having a special observation mode in which normal light and special light are alternately emitted through a turn-off period and a signal is read out from an imaging element during each turn-off period. JP2016-19569A discloses an endoscope system that acquires a special light image generated by performing imaging while a subject is irradiated with special light, and a normal light image generated by performing imaging while the subject is irradiated with normal light.

SUMMARY OF THE INVENTION

However, with the related art described above, it is not possible to display a high-quality live image based on imaging with the normal light while also performing imaging with the special light. For example, in a case in which imaging is performed while switching between the normal light and the special light, a frame rate of captured image information in a case of the normal light used for the live image is lowered, so that the frame rate of the display of the live image is lowered and it is not possible to display the high-quality live image.

In addition, in a configuration of WO2015/136963A, since normal light and special light are alternately emitted, an exposure time of the normal light is shortened, and it is not possible to display a high-quality live image. In addition, the means for solving the problems described above is not disclosed in JP2016-19569A.

The present invention has been made in view of the circumstances described above, and is to provide an endoscope system, a control method, and a non-transitory computer readable recording medium storing a control program that can display a high-quality live image based on imaging with normal light while also performing imaging with special light.

An aspect of the present invention relates to an endoscope system comprising an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, in which the imaging unit performs imaging of the imaging target at a frame rate higher than a frame rate of display of the captured image displayed by the display unit, and the light source unit repeatedly performs an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

In addition, another aspect of the present invention relates to a control method of an endoscope system including an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, the method comprising performing, by the imaging unit, imaging of the imaging target at a frame rate higher than a frame rate of display of the captured image displayed by the display unit, and repeatedly performing, by the light source unit, an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

In addition, still another aspect of the present invention relates to a non-transitory computer readable recording medium storing a control program controlling an endoscope system including an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, the program causing a computer to execute a process comprising causing the imaging unit to perform imaging of the imaging target at a frame rate higher than a frame rate of display of the captured image displayed by the display unit, and causing the light source unit to repeatedly perform an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

According to the present invention, it is possible to provide the endoscope system, the control method, and the non-transitory computer readable recording medium storing a control program that can display the high-quality live image based on imaging with the normal light while also performing imaging with the special light.

DESCRIPTION OF THE PREFERRED EMBODIMENTS

In the following, embodiments of the present invention will be described with reference to the drawings.

Figure 1:
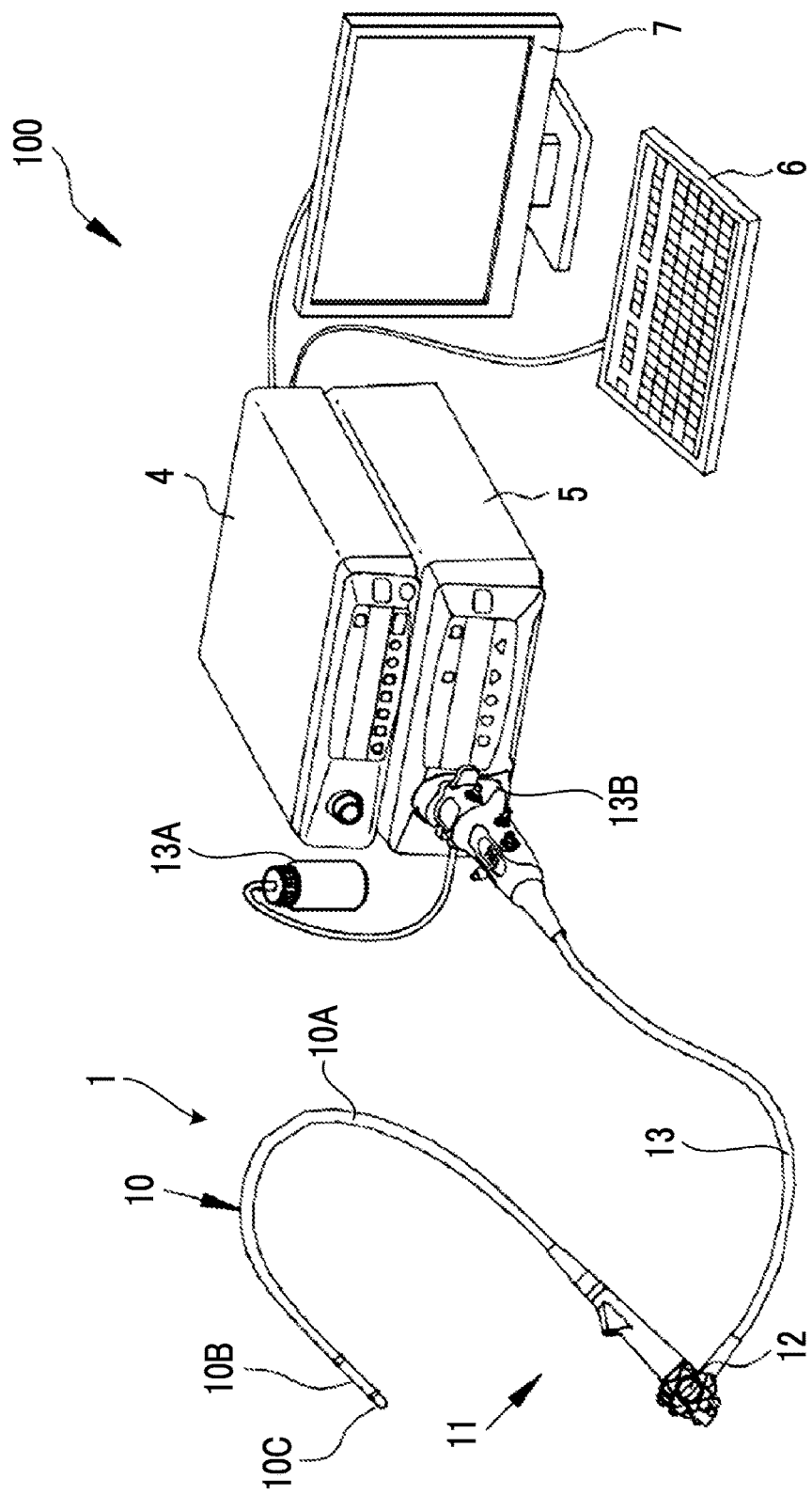
FIG. 1 is a view showing an example of an endoscope apparatus 100 which is one embodiment of the present invention.

FIG. 1 is a view showing an example of an endoscope apparatus 100 which is one embodiment of the present invention.

The endoscope apparatus 100 is an example of an endoscope system according to the embodiment of the present invention. As shown in FIG. 1, the endoscope apparatus 100 comprises an endoscope 1, and a control device 4 and a light source device 5 to which the endoscope 1 is connected. The control device 4 constitutes an imaging control unit according to the embodiment of the present invention. The light source device 5 constitutes a light source unit according to the embodiment of the present invention.

A display device 7 that displays a captured image or the like obtained by imaging an inside of a subject by the endoscope 1 and an input unit 6, which is an interface for inputting various pieces of information to the control device 4 are connected to the control device 4. The control device 4 controls the endoscope 1, the light source device 5, and the display device 7.

The display device 7 has a display surface on which display pixels are two-dimensionally arranged, and pixel data constituting image data is drawn on each display pixel on the display surface, thereby performing the display of an image based on the image data. The display device 7 constitutes a display unit that switches the display image in accordance with the command from the control device 4.

The endoscope 1 includes an insertion part 10 which is a tubular member extending in one direction and is inserted into the subject, an operating part 11 which is provided in a base end part of the insertion part 10 and includes an operation member for performing an observation mode switching operation, an imaging recording operation, a forceps operation, an air supply/water supply operation, and a suction operation, an angle knob 12 provided adjacent to the operating part 11, and a universal cord 13 including connector portions 13A and 13B that detachably connect the endoscope 1 to the control device 4 and the light source device 5, respectively.

It should be noted that, although not shown in FIG. 1, various channels, such as a forceps hole for inserting forceps for sampling a living body tissue, such as cells or polyps, an air supply/water supply channel, and a suction channel, are provided inside the operating part 11 and the insertion part 10.

The insertion part 10 is composed of a flexible part 10A having flexibility, a bendable part 10B provided at a distal end of the flexible part 10A, and a hard distal end part 10C provided at a distal end of the bendable part 10B.

The bendable part 10B is configured to be bendable by a rotational movement operation of the angle knob 12. Depending on the site of the subject in which the endoscope 1 is used, the bendable part 10B can be bent in any direction and at any angle, and the distal end part 10C can be directed in a desired direction.

Figure 2:
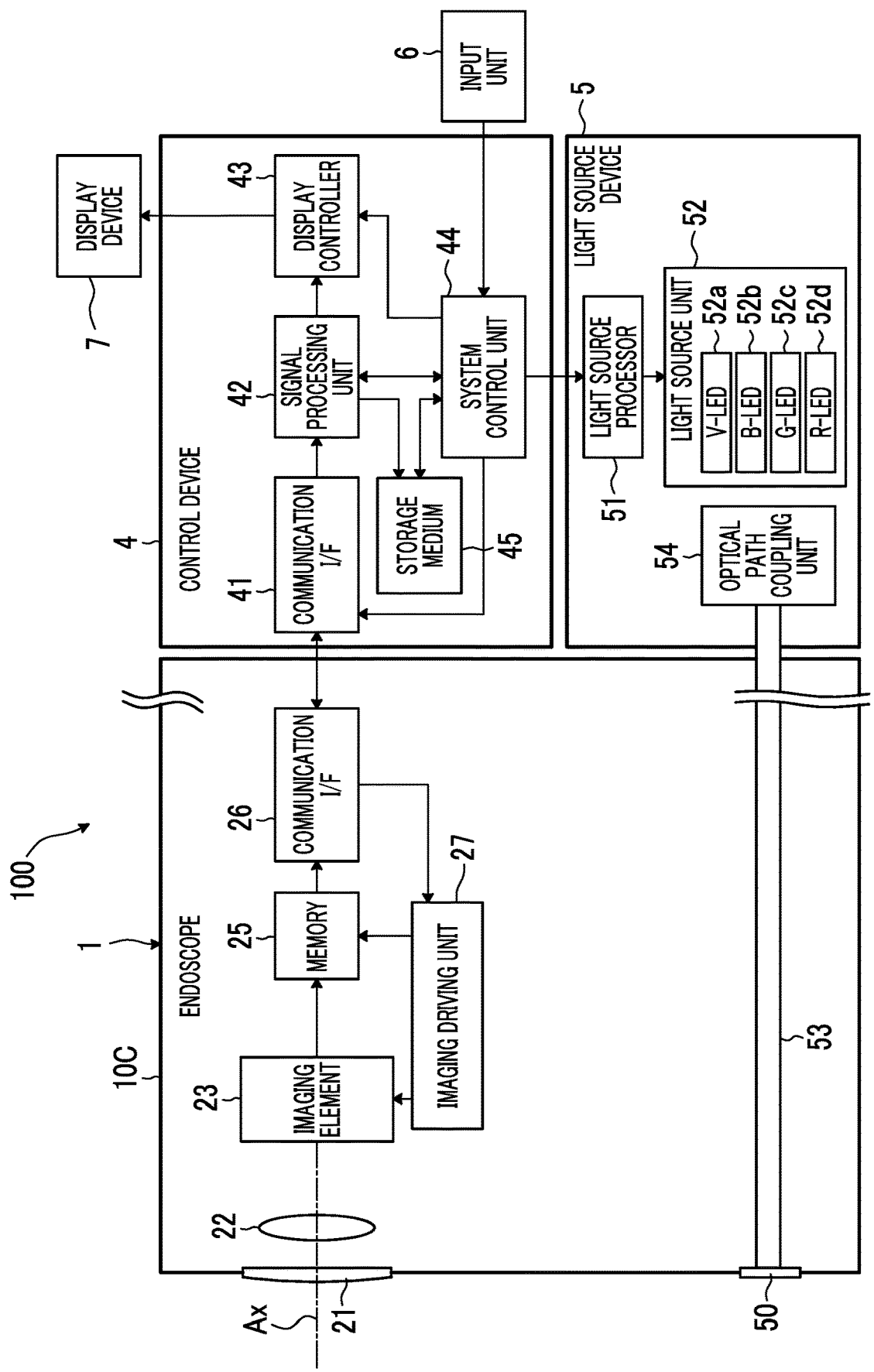
FIG. 2 is a schematic view showing an internal configuration of the endoscope apparatus 100 shown in FIG. 1.
Figure 3:
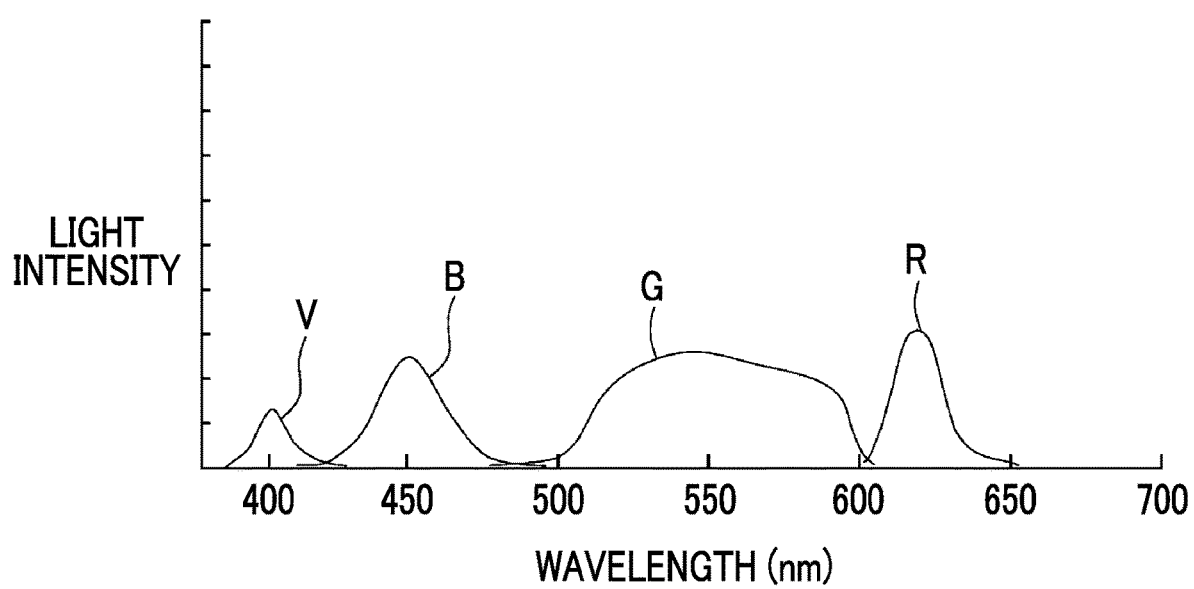
FIG. 3 is a diagram showing an example of a spectrum of light generated by a light source device 5 shown in FIG. 2.

FIG. 2 is a schematic view showing an internal configuration of the endoscope apparatus 100 shown in FIG. 1. FIG. 3 is a diagram showing an example of a spectrum of light generated by the light source device 5 shown in FIG. 2.

The light source device 5 can switch normal light and special light as illumination light and perform irradiation. The normal light is light having an emission spectrum suitable for recognition by a human, such as a doctor, such as white light. The special light is light having an emission spectrum suitable for analysis by a computer, such as IEE, which has a different emission spectrum from the normal light.

Specifically, the light source device 5 comprises a light source processor 51, a light source unit 52, and an optical path coupling unit 54. The light source processor 51 is connected to the system control unit 44 of the control device 4, and controls the light source unit 52 based on the command from the system control unit 44.

The light source unit 52 has, for example, a plurality of semiconductor light sources, each of which is turned on or off, and in a case in which the light source unit 52 is turned on, the emission amount of each semiconductor light source is controlled to emit the illumination light for illuminating an observation target. In the present embodiment, the light source unit 52 has LEDs of four colors, a violet light emitting diode (V-LED) 52a, a blue light emitting diode (B-LED) 52b, a green light emitting diode (G-LED) 52c, and a red light emitting diode (R-LED) 52d.

By independently controlling each of the V-LED 52a, the B-LED 52b, the G-LED 52c, the R-LED 52d, the light source processor 51 can emit violet light V, blue light B, green light G, or red light R by independently changing a light amount. As shown in FIG. 3, the V-LED 52a generates the violet light V of which a central wavelength is in a range of 405±10 nm and a wavelength range is in a range of 380 to 420 nm. The B-LED 52b generates the blue light B of which a central wavelength is in a range of 450±10 nm and a wavelength range is in a range of 420 to 500 nm. The G-LED 52c generates the green light G of which a wavelength range is in a range of 480 to 600 nm. The R-LED 52d generates the red light R of which a central wavelength is in a range of 620 to 630 nm and a wavelength range is in a range of 600 to 650 nm.

In addition, in a case of irradiation with the normal light, the light source processor 51 controls each of the LEDs 52a to 52d to emit the white light in which a light amount ratio of the violet light V, the blue light B, the green light G, and the red light R is Vc:Bc:Gc:Rc. It should be noted that Vc, Bc, Gc, Rc>0.

In addition, in a case of irradiation with the special light, the light source processor 51 controls each of the LEDs 52*a* to 52*d* to emit the special light in which the light amount ratio of the violet light V, the blue light B, the green light G, and the red light R as short-wavelength narrow band light is Vs:Bs:Gs:Rs.

The light amount ratio Vs:Bs:Gs:Rs is different from the light amount ratio Vc:Bc:Gc:Rc used in a case of the irradiation with the normal light, and is appropriately determined in accordance with the observation purpose. For example, in a case in which superficial blood vessels are enhanced, it is preferable to make Vs larger than Bs, Gs, and Rs, and in a case in which mesopelagic blood vessels are enhanced, it is preferable to make Gs larger than Vs, Gs, and Rs.

The optical path coupling unit 54 combines each light emitted from the V-LED 52*a*, the B-LED 52*b*, the G-LED 52*c*, and the R-LED 52*d*, and emits the combined light as the illumination light. The illumination light emitted from the optical path coupling unit 54 of the light source unit 52 enters a light guide 53 to be described below built in the universal cord 13, and is emitted to the subject through an illumination lens 50 provided at the distal end part 10C of the insertion part 10.

In the distal end part 10C of the endoscope 1, an imaging optical system including an objective lens 21 and a lens group 22, an imaging element 23 that images the subject through the imaging optical system, a memory 25, such as a random access memory (RAM), a communication interface (I/F) 26, an imaging driving unit 27, and the light guide 53 for guiding the illumination light emitted from the light source unit 52 to the illumination lens 50 are provided. The imaging element 23 constitutes an imaging unit according to the embodiment of the present invention.

The light guide 53 extends from the distal end part 10C to the connector portion 13A of the universal cord 13. The illumination light emitted from the light source unit 52 of the light source device 5 can enter the light guide 53 in a state in which the connector portion 13A of the universal cord 13 is connected to the light source device 5.

A charge coupled device (CCD) image sensor or a complementary metal oxide semiconductor (CMOS) image sensor is used as the imaging element 23. In the present embodiment, the imaging element 23 is the CMOS using a rolling shutter.

The imaging element 23 has a light-receiving surface on which a plurality of pixels are two-dimensionally arranged, and converts an optical image formed on the light-receiving surface by the imaging optical system described above into an electrical signal (imaging signal) in each pixel. Moreover, the imaging element 23 converts the converted imaging signal from an analog signal into a digital signal having a predetermined number of bits, and outputs the imaging signal converted into the digital signal to the memory 25. For example, an imaging element on which a color filter, such as an elementary color or a complementary color, is mounted, is used as the imaging element 23. A set of the imaging signals output from the pixels of the light-receiving surface of the imaging element 23 is referred to as a captured image signal.

The imaging element 23 may be disposed at the distal end part 10C in a state in which the light-receiving surface is perpendicular to an optical axis Ax of the objective lens 21, or may be disposed at the distal end part 10C in a state in which the light-receiving surface is parallel to the optical axis Ax of the objective lens 21.

The imaging optical system provided in the endoscope 1 is composed of optical members (including the lens group 22 described above), such as a lens and a prism, which are present on an optical path of the light from the subject between the imaging element 23 and the objective lens 21, and the objective lens 21. There is also a case in which the imaging optical system is composed of only the objective lens 21.

The memory 25 transitorily records the digital imaging signal output from the imaging element 23.

The communication I/F 26 is connected to a communication interface (I/F) 41 of the control device 4. The communication I/F 26 transmits the imaging signal recorded in the memory 25 to the control device 4 through a signal line in the universal cord 13.

The imaging driving unit 27 is connected to the system control unit 44 of the control device 4 via the communication I/F 26. The imaging driving unit 27 drives the imaging element 23 and the memory 25 based on the command from the system control unit 44 received by the communication I/F 26.

The control device 4 comprises the communication I/F 41, which is connected to the communication I/F 26 of the endoscope 1 by the universal cord 13, a signal processing unit 42, a display controller 43, the system control unit 44, and a recording medium 45.

The communication I/F 41 receives the imaging signal transmitted from the communication I/F 26 of the endoscope 1 to transmit the imaging signal to the signal processing unit 42.

The signal processing unit 42 has a memory that transitorily records the imaging signal received from the communication I/F 41 built therein, and performs processing (image processing, such as demosaic processing or gamma-correction processing) on the captured image signal that is a set of the imaging signals recorded in the memory to generate captured image information in such a format that recognition processing to be described below or the like can be performed. The captured image information generated by the signal processing unit 42 is recorded on the recording medium 45, such as a hard disk or a flash memory.

The display controller 43 displays a captured image based on the captured image information generated by the signal processing unit 42 on the display device 7. A coordinate of each pixel data constituting the captured image information generated by the signal processing unit 42 is managed in association with a coordinate of any of the display pixels constituting the display surface of the display device 7.

The system control unit 44 controls each unit of the control device 4, and transmits the command to the imaging driving unit 27 of the endoscope 1 and the light source processor 51 of the light source device 5, and integrally controls the entire endoscope apparatus 100. For example, the system control unit 44 performs the control of the imaging element 23 via the imaging driving unit 27. In addition, the system control unit 44 performs the control of the light source unit 52 via the light source processor 51.

The system control unit 44 or the signal processing unit 42 includes various processors that execute a program to perform processing, a RAM, and a read only memory (ROM).

Examples of various processors include a central processing unit (CPU), which is a general-purpose processor that executes the program to perform various pieces of processing, a programmable logic device (PLD), which is a processor of which the circuit configuration can be changed after the manufacture, such as a field programmable gate array (FPGA), and a dedicated electric circuit, which is a processor having the circuit configuration specially designed for executing specific processing, such as an application specific integrated circuit (ASIC).

More specifically, the structure of these various processors is an electric circuit in which circuit elements, such as semiconductor elements, are combined.

The system control unit 44 or the signal processing unit 42 may be composed of one of the various processors, or may be composed of a combination (for example, a combination of a plurality of FPGAs or a combination of a CPU and an FPGA) of two or more processors of the same type or different types.

Figure 4:
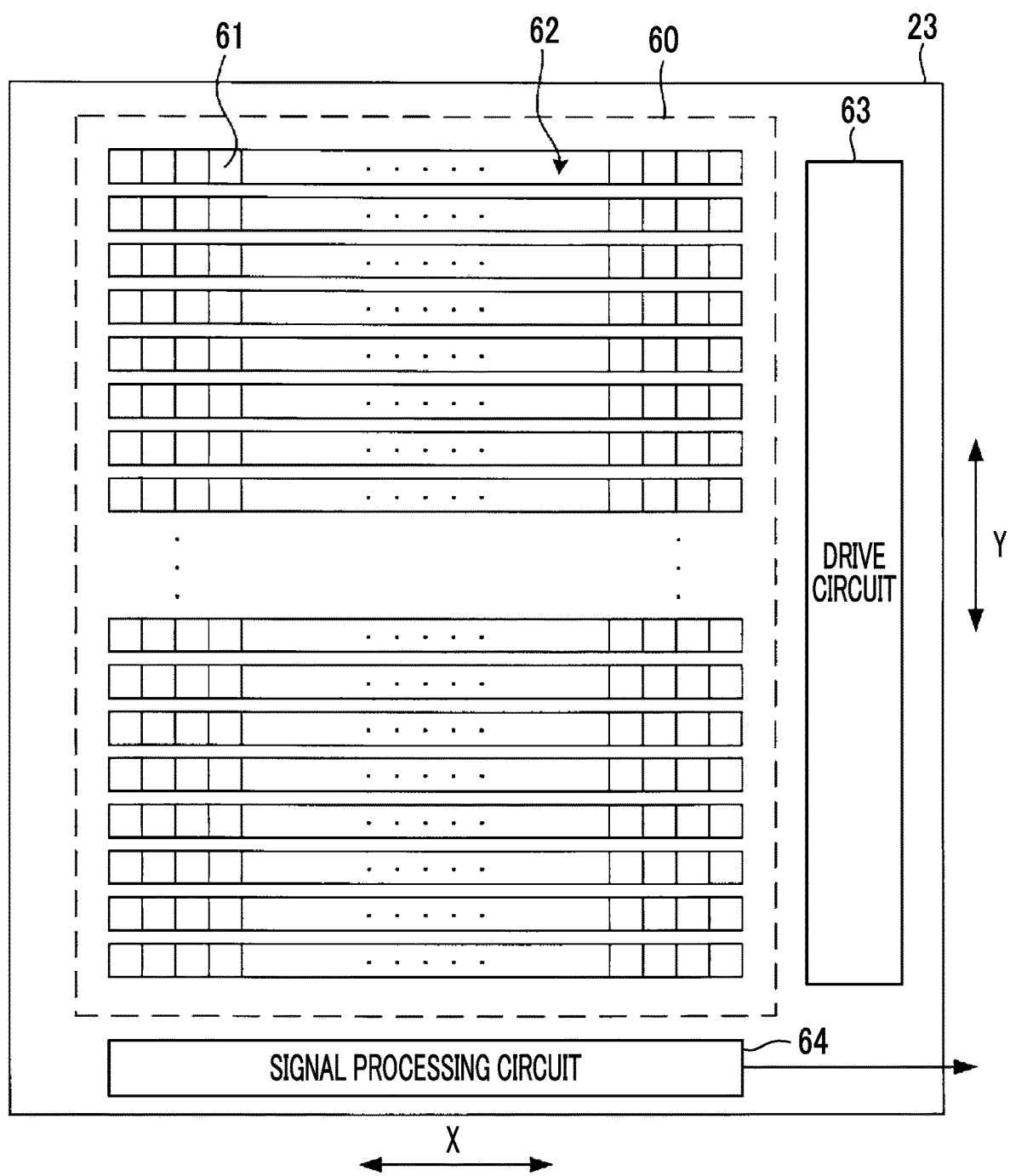
FIG. 4 is a schematic plan view showing a schematic configuration of an imaging element 23 shown in FIG. 2.

FIG. 4 is a schematic plan view showing a schematic configuration of the imaging element 23 shown in FIG. 2.

The imaging element 23 comprises an imaging surface 60 on which a plurality of pixel rows 62 consisting of a plurality of pixels 61 arranged in a row direction X are arranged in a column direction Y orthogonal to the row direction X, a drive circuit 63 that drives the pixels 61 arranged on the imaging surface 60, and a signal processing circuit 64 that processes the pixel signal read out from each pixel 61 of the pixel row 62 arranged on the imaging surface 60 into the signal line. The imaging surface 60 constitutes the light-receiving surface.

In the following, in FIG. 4, an end portion of the imaging surface 60 on one end side (upper side in FIG. 4) in the column direction Y is referred to as an upper end, and an end portion of the imaging surface 60 on the other end side (lower side in FIG. 4) in the column direction Y is referred to as a lower end.

The drive circuit 63 shown in FIG. 4 independently drives each pixel row 62 based on the signal from the imaging driving unit 27, and performs the reset of each pixel 61 included in the pixel row 62 (discharge of charge accumulated in the photoelectric conversion element), the reading out of the pixel signal in accordance with the charge accumulated in the photoelectric conversion element of each pixel 61 into the signal line, and the like.

The signal processing circuit 64 shown in FIG. 4 performs sampling two correlation pile processing on the pixel signal read out from each pixel 61 of the pixel row 62 into the signal line, converts the pixel signal subjected to the sampling two correlation pile processing into the digital signal, and outputs the converted pixel signal. The signal processing circuit 64 is controlled by the imaging driving unit 27.

The signal processing unit 42 performs the signal processing, such as the demosaic processing and the gamma correction processing, on the pixel signal output from the imaging element 23 to generate the captured image information.

The endoscope apparatus 100 is equipped with a continuous imaging mode that continuously generates a plurality of pieces of the captured image information in accordance with one imaging instruction. In the continuous imaging mode, the system control unit 44 drives the imaging element 23 by the imaging driving unit 27 by a rolling shutter system to image the subject.

The driving of the rolling shutter system includes the rolling reset driving and the rolling read-out driving. The rolling reset driving is driving in which processing of resetting each pixel 61 of the pixel row 62 and starting the exposure of each pixel 61 is sequentially performed while changing the pixel row 62. The rolling read-out driving is driving in which processing of reading out the signal from each pixel 61 of the exposed pixel row 62 and terminating the exposure of the pixel row 62 is sequentially performed while changing the pixel row 62.

Figure 5:
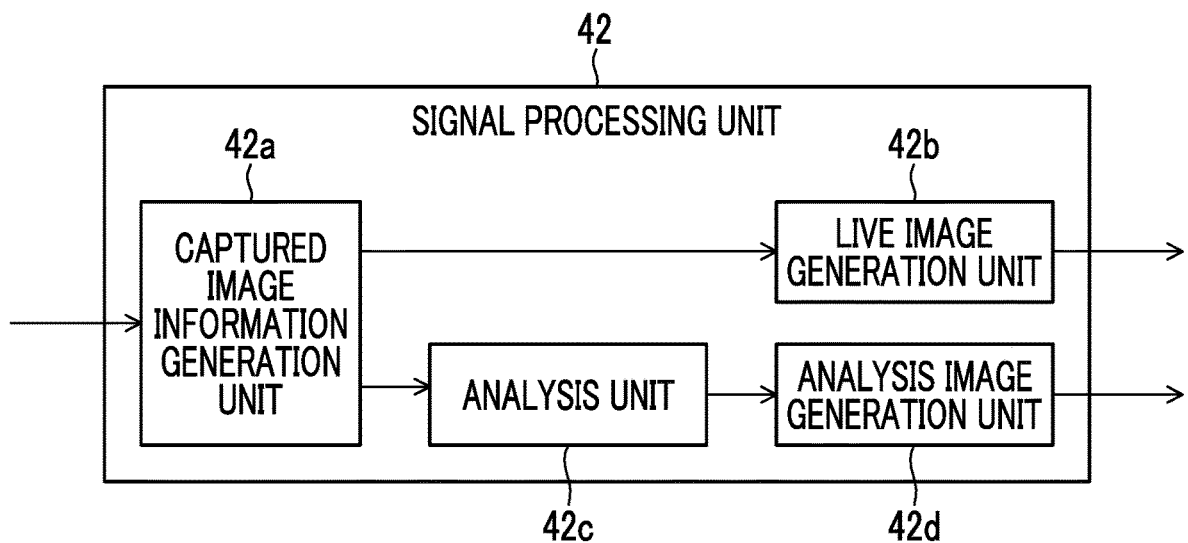
FIG. 5 is a diagram showing an example of functional blocks of a system control unit 44 of a signal processing unit 42 shown in FIG. 2.

FIG. 5 is a diagram showing an example of functional blocks of the system control unit 44 of the signal processing unit 42 shown in FIG. 2.

A processor of the signal processing unit 42 executes a control program stored in the ROM built in the signal processing unit 42 to function as a control device comprising a captured image information generation unit 42a, a live image generation unit 42b, an analysis unit 42c, and an analysis image generation unit 42d.

The captured image information generation unit 42a generates the captured image information by performing the image processing, such as the demosaic processing or the gamma correction processing, on the imaging signal obtained by imaging of the imaging element 23. The captured image information generation unit 42a outputs the captured image information based on the imaging signal obtained by imaging during the irradiation with the normal light to the live image generation unit 42b as an imaging frame in the generated captured image information, and outputs the captured image information based on the imaging signal obtained by imaging during the irradiation with the special light to the analysis unit 42c as an imaging frame. The imaging frame is the imaging signal obtained by one imaging.

The live image generation unit 42b generates live image information for displaying the live image based on the imaging frame output from the captured image information generation unit 42a, and outputs the generated live image information to the display controller 43 (see FIG. 2) as the captured image information. The live image is an image (motion picture) that displays a result of continuous imaging by the imaging element 23 in real time, and constitutes the captured image according to the embodiment of the present invention.

The analysis unit 42c performs the analysis based on the imaging frame output from the captured image information generation unit 42a, and outputs a result of the analysis to the analysis image generation unit 42d. Here, the analysis image generation unit 42d performs processing of extracting a contour of the captured image as the analysis.

For example, the analysis unit 42c specifies the contour of a biological structure reflected in the image indicated by the captured image information obtained by imaging during the irradiation with the special light. Examples of the biological structure of a specific target include a superficial blood vessel structure, a middle layer blood vessel structure, or a deep blood vessel structure. The analysis image generation unit 42d generates image information for displaying a contour-enhanced image in which the contour specified by the analysis unit 42c is enhanced in the image indicated by the captured image information obtained by imaging during the irradiation with the special light. As a result, the contour-enhanced image is displayed on a sub-screen 72, and the operator of the endoscope 1 can easily recognize the structure inside the subject.

The analysis image generation unit 42d generates IEE image information for displaying an IEE image indicating the result of the analysis output from the analysis unit 42c, and outputs the generated IEE image information to the display controller 43 (see FIG. 2) as the captured image information. The IEE image is an image in which the contour of the structure of the subject is enhanced based on the imaging signal obtained by imaging during the irradiation with the special light, such as a blue laser. In this case, the special light, such as the blue laser, constitutes light for image-enhanced endoscopy. For example, the IEE image is an image in which the surface blood vessel structure is enhanced, an image in which the middle layer blood vessel structure is enhanced, an image in which the deep blood vessel structure is enhanced, and the like.

It should be noted that the image generated by the analysis image generation unit 42d is not limited to the captured image and the processed image of the captured image, and may be an image indicating the numerical value (number or accuracy) or the text (type of tumor) based on the analysis by the analysis unit 42c.

As described with reference to FIG. 5, the endoscope apparatus 100 comprises the analysis unit 42c that performs the analysis based on the captured image information obtained by imaging in a second period in which the special light is emitted in the captured image information. On the other hand, the endoscope apparatus 100 displays the live image based on the captured image information obtained by imaging in a first period in which the normal light is emitted in the captured image information. As a result, it is possible to perform the analysis based on the special light while displaying the live image based on the normal light.

Figure 6:
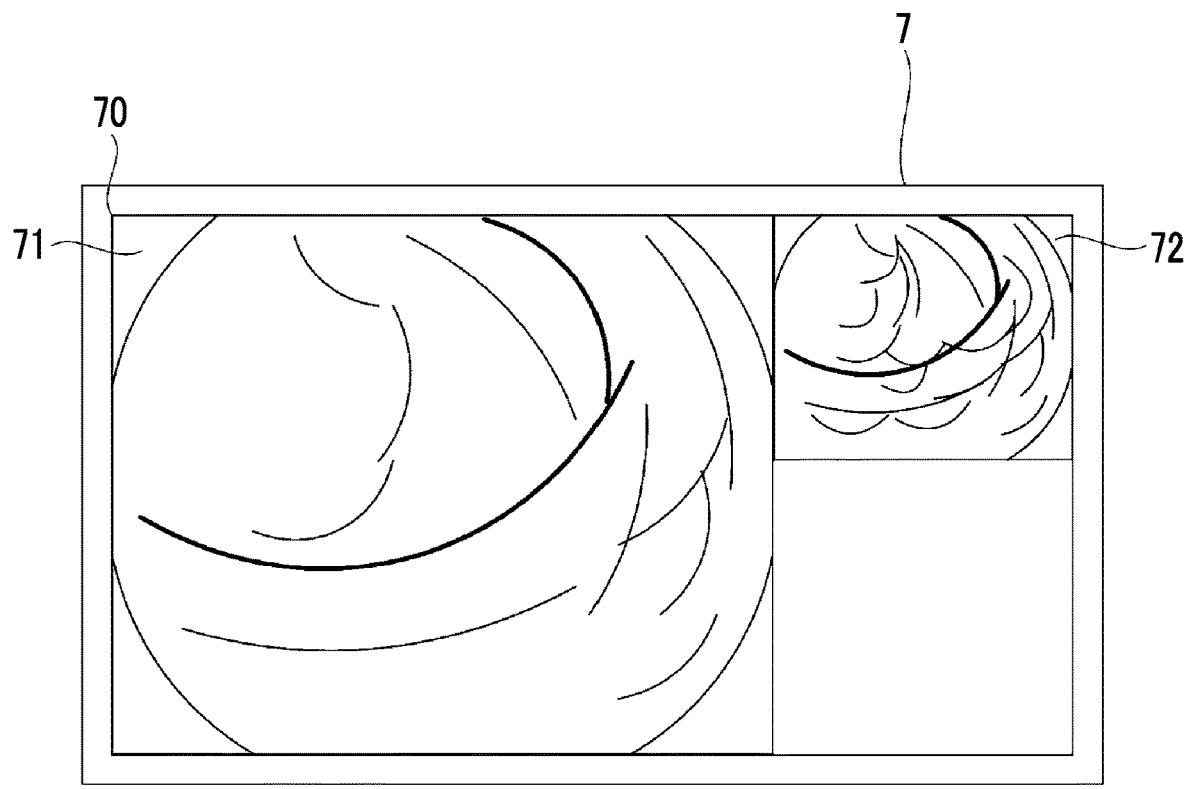
FIG. 6 is a diagram showing an example of a screen displayed on a display device 7.

FIG. 6 is a diagram showing an example of a screen displayed on the display device 7.

The display controller 43 displays, for example, a screen 70 shown in FIG. 6 on the display device 7 based on the captured image information output from the signal processing unit 42. The screen 70 includes a main screen 71 and the sub-screen 72.

The live image based on the live image information output from the live image generation unit 42b of the signal processing unit 42 is displayed on the main screen 71. The IEE image based on the IEE image information output from the analysis image generation unit 42d of the signal processing unit 42 is displayed on the sub-screen 72.

As described with reference to FIG. 6, the endoscope apparatus 100 displays the screen 70 including the live image based on the captured image information obtained by imaging in the first period in which the normal light is emitted, and the result of the analysis based on the captured image information obtained by imaging in the second period in which the special light is emitted.

Figure 7:
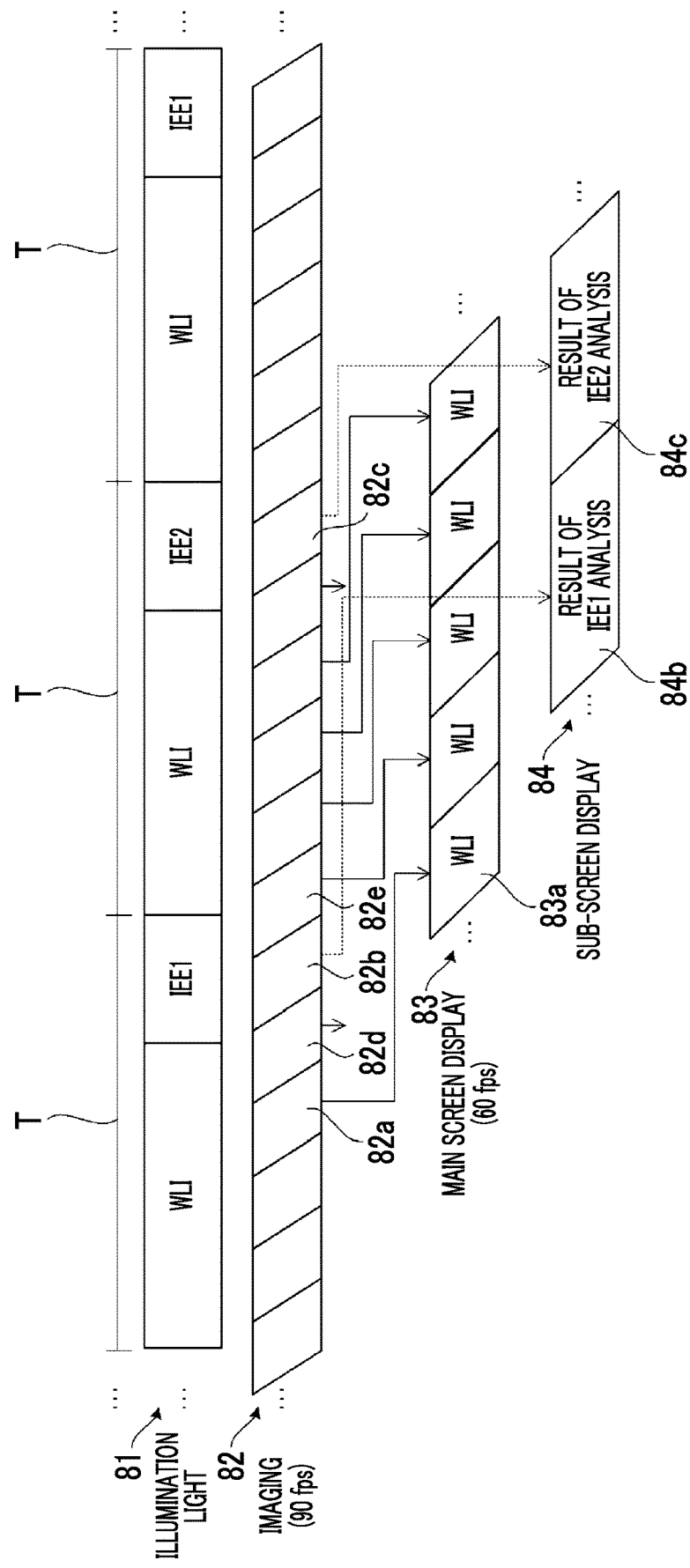
FIG. 7 is a diagram showing an example of a time chart of each operation in the endoscope apparatus 100.

FIG. 7 is a diagram showing an example of a time chart of each operation in the endoscope apparatus 100.

An illumination light timing 81 is a timing at which the light source device 5 emits the illumination light in accordance with the command from the control device 4. The WLI in the illumination light timing 81 is a timing at which the light source device 5 emits the normal light, such as the white light, as the illumination light. The IEE1 in the illumination light timing 81 is a timing at which the light source device 5 emits first special light, such as narrow band light, as the illumination light. The IEE2 in the illumination light timing 81 is a timing at which the light source device 5 emits second special light different from the first special light as the illumination light.

As shown in the illumination light timing 81, the light source device 5 repeatedly executes a predetermined irradiation operation in a period T. The irradiation operation is an operation of emitting the normal light and then emitting the special light (first special light or second special light). In the example shown in FIG. 7, the light source device 5 alternately switches the special light to be emitted between the first special light and the second special light for each period T. It should be noted that the light source device 5 may emit only the first special light for each period T.

An imaging timing 82 is a timing at which the imaging element 23 performs imaging (exposure) in accordance with the command from the control device 4. A vertical direction at the imaging timing 82 indicates a position of the pixel row 62 in the column direction Y (see FIG. 4). As described above, since the imaging element 23 in the present embodiment performs imaging of the rolling shutter system, the imaging timing 82 deviates for each pixel row 62. In the example shown in FIG. 7, the imaging element 23 performs imaging at a frame rate of 90 frames per second (fps).

As shown in the illumination light timing 81 and the imaging timing 82, the first period in which the light source device 5 continuously emits the normal light extends over a plurality of consecutive frames in imaging by the imaging element 23. In addition, the second period in which the light source device 5 continuously emits the special light extends over at least one frame in imaging by the imaging element 23. In the example shown in FIG. 7, the second period extends over the plurality of consecutive frames in imaging by the imaging element 23.

A main screen display timing 83 is a timing at which the display device 7 displays (draws) the main screen 71 in accordance with the command from the control device 4. In the example shown in FIG. 7, the display device 7 displays the main screen 71 at 60 fps, that is, a frame rate lower than the frame rate of imaging by the imaging element 23. A sub-screen display timing 84 is a timing at which the display device 7 displays (draws) the sub-screen 72 in accordance with the command from the control device 4.

As shown in the illumination light timing 81, the imaging timing 82, and the main screen display timing 83, the display device 7 is displays the main screen 71 based on the imaging signal obtained by imaging during the irradiation with the normal light in imaging indicated at the imaging timing 82. For example, the display device 7 performs main screen display 83a based on the imaging signal obtained by imaging 82a.

In addition, as shown in the illumination light timing 81, the imaging timing 82, and the sub-screen display timing 84, the display device 7 is displays the sub-screen 72 based on the imaging signal obtained by imaging during the irradiation with the special light in imaging indicated at the imaging timing 82. For example, the display device 7 performs sub-screen display 84b (display of a result of the IEE1 analysis) based on the imaging signal obtained by imaging 82b during the irradiation with the first special light (IEE1). In addition, the display device 7 performs sub-screen display 84c (display of a result of the IEE2 analysis) based on the imaging signal obtained by imaging 82c during the irradiation with the second special light (IEE2).

In addition, the control device 4 performs blank reading of the imaging signal obtained by the imaging including the timing when the illumination light emitted by the light source device 5 is switched from the normal light to the special light in imaging indicated at the imaging timing 82. The blank reading of the imaging signal means that the image based on the imaging signal is not displayed by the display device 7, for example, the imaging signal is discarded. For example, the control device 4 reads out the pixel signal in accordance with the charge accumulated in the photoelectric conversion element into the signal line, and discards the read out signal while discharging the charge accumulated in the photoelectric conversion element in the same manner as the reset described above. It should be noted that the read out signal may be discarded by the endoscope 1 or the control device 4.

For example, the control device 4 discards the imaging signal obtained by imaging 82*d*. As a result, even in a case in which a global reset is not performed at the timing when the illumination light emitted by the light source device 5 is switched from the normal light to the special light, the influence of the switching of the illumination light on the analysis described above or the display of the main screen 71 can be suppressed.

For example, in a case in which the imaging signal obtained by imaging including the timing when the illumination light is switched from the normal light to the special light is used for the analysis described above, the analysis described above is not performed correctly due to the switching of the illumination light, and the content of the analysis result image displayed on the sub-screen 72 is inaccurate. In addition, in a case in which the imaging signal obtained by imaging including the timing when the illumination light is switched from the normal light to the special light is used for the main screen 71, the color of the live image displayed on the main screen 71 is transitorily changed due to the switching of the illumination light. By performing the blank reading described above, it is possible to suppress the influence on the display of the main screen 71 or the sub-screen 72.

Although not shown, the control device 4 may further perform the blank reading of the imaging signal obtained by the imaging including the timing when the illumination light emitted by the light source device 5 is switched from the special light to the normal light in imaging at each timing indicated at the imaging timing 82. For example, the control device 4 may discard the imaging signal obtained by imaging 82*e*. As a result, even in a case in which the global reset is not performed at the timing when the illumination light emitted by the light source device 5 is switched from the special light to the normal light, the influence of the switching of the illumination light on the analysis described above or the display of the main screen 71 can be suppressed.

As described with reference to FIG. 7, the imaging element 23 performs imaging at a frame rate higher than the frame rate of the display by the display device 7, so that the reduction of the frame rate of the display of the live image due to the switching between the normal light and the special light can be suppressed, and the high-quality live image can be displayed.

In addition, since the first period in which the light source device 5 continuously emits the normal light is longer than the second period in which the light source device 5 continuously emits the special light, for example, it is possible to lengthen the exposure time during the irradiation with the normal light and display the high-quality live image as compared with a configuration in which the normal light and the special light are alternately switched for each frame in imaging by the imaging element 23.

In addition, by performing the blank reading described above at the timing when the illumination light emitted by the light source device 5 is switched, for the imaging signal immediately after the start of the second period in which the light source device 5 continuously emits the special light, at least the imaging signal excluding the imaging signal for one frame by the imaging element 23 can be acquired as the imaging signal displayed as the sub-screen 72 of the display device 7. As a result, even in a case in which the global reset is not performed at the timing when the illumination light emitted by the light source device 5 is switched, the influence of the switching of the illumination light on the reset of the analysis can be suppressed.

Since it is not necessary to perform the global reset, it is not necessary to provide a global reset circuit in the imaging element 23 even in a configuration in which imaging of the rolling shutter system is performed, and the circuit scale can be suppressed.

As described above, in the endoscope apparatus 100, the imaging element 23 performs imaging at a frame rate higher than the frame rate of the display of the captured image displayed by the display device 7. Moreover, the light source device 5 repeatedly performs the operation of continuously emitting the illumination light in the first period over the plurality of consecutive frames in imaging by the imaging element 23, and then emitting the illumination light having a spectrum different from the spectrum of the illumination light emitted in the first period in a second period which is the period over at least one frame in imaging by the imaging element 23. As a result, it is possible to display the high-quality live image based on imaging with the normal light while performing the imaging with the special light without the operation of switching the illumination light by the user.

Figure 8:
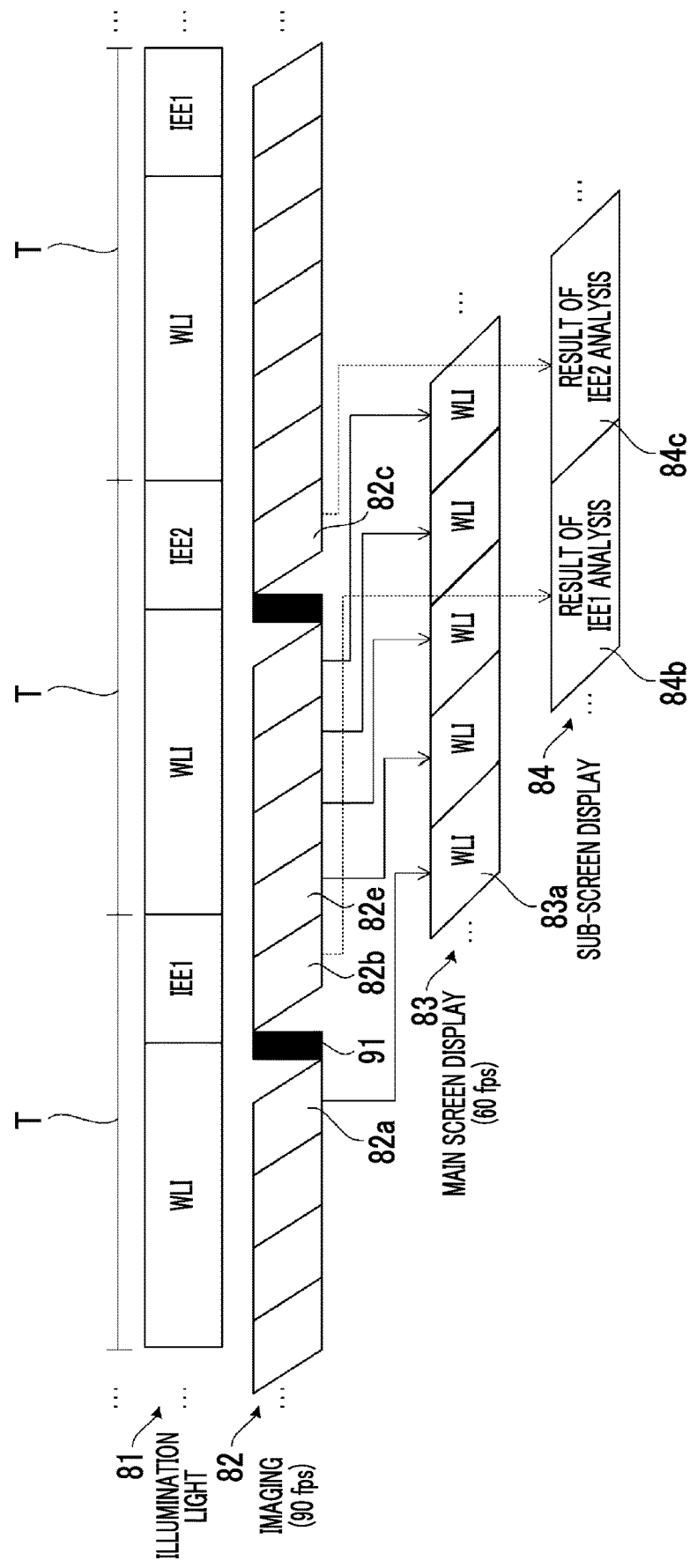
FIG. 8 is a diagram showing an example of a time chart of each operation in a first modification example of the endoscope apparatus 100.

FIG. 8 is a diagram showing an example of a time chart of each operation in a first modification example of the endoscope apparatus 100.

Although the configuration has been described in which the global reset is not performed in the imaging element 23 by performing the blank reading, a configuration may be adopted in which the global reset is performed. In the imaging timing 82 of FIG. 8, the black rectangle indicates the timing at which the global reset of the imaging element 23 is performed.

In the example shown in FIG. 8, the imaging element 23 performs the global reset instead of the blank reading described above at the timing when the illumination light emitted by the light source device 5 switches from the normal light to the special light. For example, the imaging element 23 performs a global reset 91 at a timing between the imaging 82*a* and the imaging 82*b*. As a result, even in a case in which the blank reading described above is not performed at the timing when the illumination light emitted by the light source device 5 is switched from the normal light to the special light, the influence of the switching of the illumination light on the analysis described above or the display of the main screen 71 can be suppressed.

Although not shown, the control device 4 may further perform the global reset at the timing when the imaging element 23 switches the illumination light emitted by the light source device 5 from the special light to the normal light. For example, the control device 4 may perform the global reset instead of the imaging 82*e*. As a result, even in a case in which the blank reading is not performed at the timing when the illumination light emitted by the light source device 5 is switched from the special light to the normal light, the influence of the switching of the illumination light on the analysis described above or the display of the main screen 71 can be suppressed.

As shown in FIG. 8, the global reset of the imaging element 23 is performed after the first period in which the normal light is emitted, and the captured image information after the global reset is performed is acquired as the captured image information of the second period in which the special light is emitted. As a result, the influence of the switching of the illumination light on the result of the analysis can be suppressed.

Figure 9:
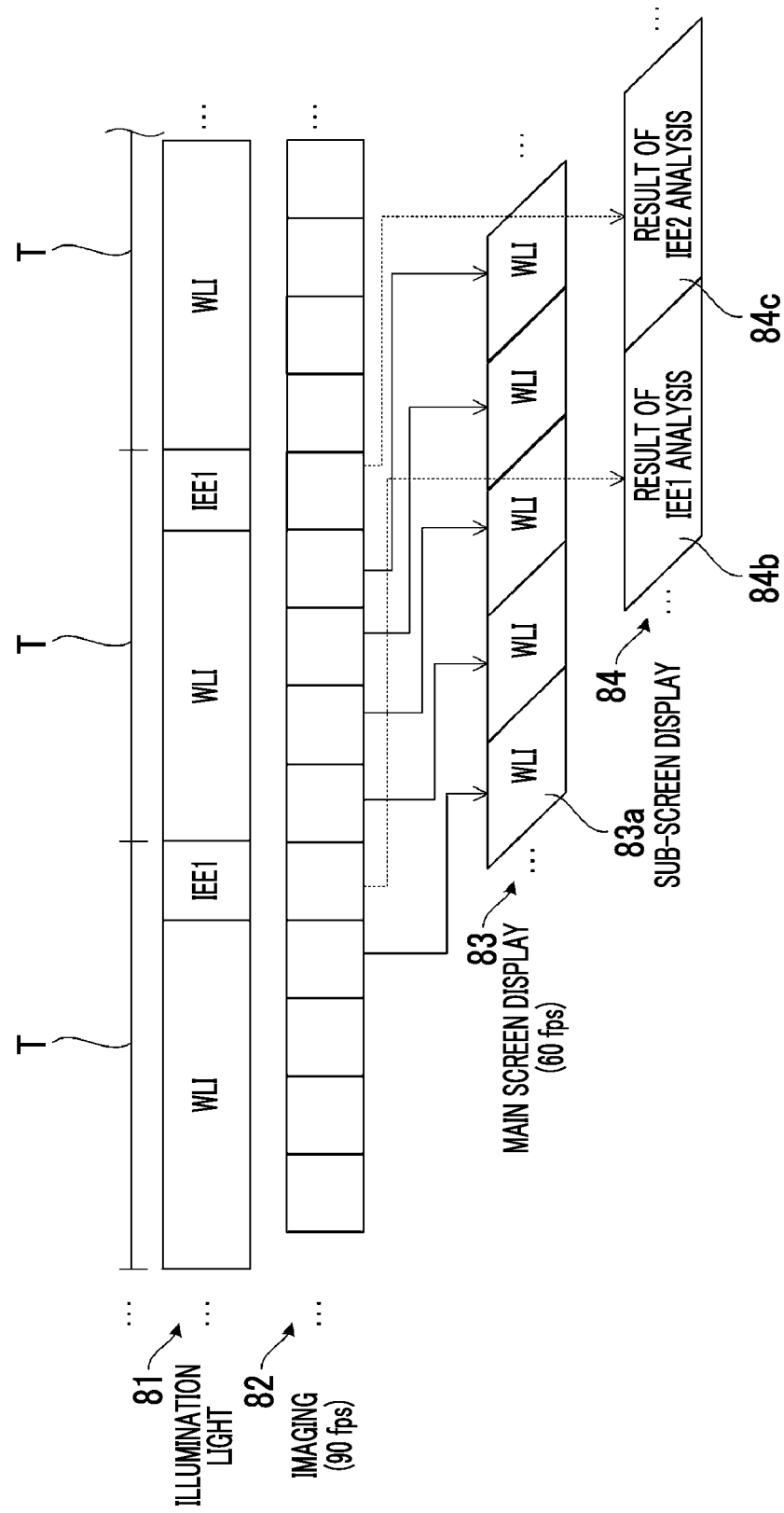
FIG. 9 is a diagram showing an example of a time chart of each operation in a second modification example of the endoscope apparatus 100.

FIG. 9 is a diagram showing an example of a time chart of each operation in a second modification example of the endoscope apparatus 100.

Although the configuration has been described in which the imaging element 23 performs imaging of the rolling shutter system, a configuration may be adopted in which the imaging element 23 performs imaging of the global shutter system. The imaging timing 82 in FIG. 9 indicates the timing of imaging (exposure) in a case in which the imaging element 23 performs imaging of the global shutter system. As shown in the imaging timing 82 of FIG. 9, in the global shutter system, the imaging timing is the same for each pixel row 62.

In this case, as shown in FIG. 9, the light source device 5 switches the illumination light in imaging of the global shutter system. As a result, even in a case in which the global reset or the blank reading described above is not performed, it is possible to suppress the influence of the switching of the illumination light on the analysis described above or the display of the main screen 71. As shown in FIG. 9, the imaging element 23 may perform the imaging operation of the global shutter system.

(Another Example of Analysis)

Although the extraction of the contour of the captured image has been described as the analysis by the analysis unit 42c (signal processing unit 42) based on the image captured image information obtained by imaging during the irradiation with the special light, the analysis by the analysis unit 42c is not limited to this.

For example, the analysis unit 42c may analyze an insertion shape of the endoscope 1 as the analysis described above. Specifically, the analysis of the insertion shape of the endoscope 1 is specifying of the insertion shape of the insertion part 10 of the endoscope 1 inserted into the subject. For example, the analysis unit 42c specifies the insertion shape of the endoscope 1 based on the change in the captured image information obtained by imaging during the irradiation with the special light. The analysis image generation unit 42d generates image information for displaying an image indicating the insertion shape of the endoscope 1 specified by the analysis unit 42c. As a result, the image indicating the insertion shape of the endoscope 1 is displayed on the sub-screen 72, so that the operator of the endoscope 1 can easily insert the insertion part 10 of the endoscope 1 into the subject.

Alternatively, the analysis unit 42c may detect a region-of-interest inside the subject into which the endoscope 1 is inserted as the analysis described above. For example, the analysis unit 42c detects the region-of-interest inside the subject from the image indicated by the captured image information obtained by imaging during the irradiation with the special light. The region-of-interest is a region that is recommended for attention in the observation of the inside of the subject, such as a region that is likely to be a lesion. The analysis image generation unit 42d generates image information for displaying a region-of-interest-enhanced image in which the region-of-interest detected by the analysis unit 42c is enhanced in the image indicated by the captured image information obtained by imaging during the irradiation with the special light. As a result, the region-of-interest-enhanced image is displayed on a sub-screen 72, and the operator of the endoscope 1 can easily recognize the region-of-interest inside the subject. Alternatively, the analysis image generation unit 42d may generate image information for displaying color difference-expanded image subjected to color difference expansion processing of expanding a color difference between an abnormal site (lesion site), which is the region-of-interest, and a normal site in the image indicated by the captured image information obtained by imaging during the irradiation with the special light. As a result, the color difference-expanded image is displayed on the sub-screen 72, and the operator of the endoscope 1 can easily distinguish between the abnormal site and the normal site inside the subject.

Alternatively, the analysis unit 42c may select a similar case image as the analysis described above. For example, the analysis unit 42c selects a case image similar to the captured image information obtained by imaging during the irradiation with the special light by searching a database accessible to the endoscope apparatus 100. The analysis image generation unit 42d generates image information for displaying an image indicating a selection result by the analysis unit 42c. The selection result by the analysis unit 42c may be the case image itself selected by the analysis unit 42c, or may be information, such as diagnosis result, relating to the case image associated with the case image selected by the analysis unit 42c in the database. As a result, the selection result of the similar case image is displayed on the sub-screen 72, and the operator of the endoscope 1 can easily compare a state inside the subject under observation with the similar case.

Alternatively, the analysis unit 42c may perform determination of a tumor and a non-tumor as the analysis described above. For example, the analysis unit 42c determines whether or not a biological region reflected in the image indicated by the image captured image information obtained by imaging during the irradiation with the special light is the tumor. The analysis image generation unit 42d generates image information for displaying an image indicating a determination result by the analysis unit 42c. The determination result by the analysis unit 42c may be information indicating whether or not the biological region reflected in the most recently captured image is the tumor, or may be information indicating the number of the biological regions determined to be the tumor from the start of the current examination. As a result, the determination result of the tumor and the non-tumor is displayed on the sub-screen 72, and it is possible to support the observation or the operation of the endoscope 1 by the operator of the endoscope 1.

Alternatively, the analysis unit 42c may specify a state of an organ as the analysis described above. For example, the analysis unit 42c specifies the state of the organ reflected in the image indicated by the captured image information obtained by imaging during the irradiation with the special light. Examples of the state of the organ include the oxygen saturation for each region, the thickness, the density, pattern, and the uniformity of the vessel structure, the surface structure of the large intestine (for example, pit pattern structure), or the surface structure of the duodenum (for example, villous structure). The analysis image generation unit 42d generates image information for displaying an image indicating a specifying result by the analysis unit 42c. For example, the analysis image generation unit 42d generates an oxygen saturation image obtained by imaging the oxygen saturation for each specified region. As a result, the specifying result of the state of the organ is displayed on the sub-screen 72, and it is possible to support the observation or the operation of the endoscope 1 by the operator of the endoscope 1.

Alternatively, the analysis unit 42c may generate a planned separation line as the analysis described above. For example, the analysis unit 42c decides the planned separation line (demarcation line) which is the line to be separated to remove the tumor in the biological region reflected in the image indicated by the captured image information obtained by imaging during the irradiation with the special light. The analysis image generation unit 42d generates image information for displaying an image to which the planned separation line decided by the analysis unit 42c is attached in the image indicated by the captured image information obtained by imaging during the irradiation with the special light. As a result, the image to which the planned separation line is attached is displayed on the sub-screen 72, and the operator of the endoscope 1 can easily recognize the planned separation line inside the subject.

(Modification Example of First Period, Second Period, and Period T)

Although the configuration has been described in which the length of each of the first period in which the normal light is emitted and the second period in which the special light is emitted is fixed in the repetition for each period T, but the length of each of the first period in which the normal light is emitted and the second period in which the special light is emitted does not have to be fixed (may be variable) in the repetition for each period T. For example, a ratio of the lengths of the first period and the second period in one period T may be 3:1, and a ratio of the lengths of the first period and the second period in the other period T may be 3:2.

In addition, although the case has been described in which the period T, which is the repetition period of the operation of emitting the normal light and the special light, is fixed, the period T may be variable. In addition, the configuration has been described in which the normal light is first emitted and then the special light is emitted in the period T, a configuration may be adopted in which the special light is first emitted and then the normal light is emitted in the period T.

In addition, the spectrum of the normal light may be fixed in the repetition for each period T or may be variable in the repetition for each period T. Similarly, the spectrum of the special light may be fixed in the repetition for each period T or may be variable in the repetition for each period T.

In addition, although the configuration has been described in which the second period in which the special light is emitted is immediately after the first period in which the normal light is emitted, a non-irradiation period in which the light source device 5 does not emit the illumination light may be present between the first period and the second period.

In addition, a configuration may be adopted in which narrow band short wavelength dimming light and white light are simultaneously emitted as the normal light or the special light described above. As a result, minute differences in color are enhanced and displayed, the observation, such as inflammation observation or pick-up observation, is facilitated.

(Another Embodiment of Endoscope System)

The endoscope apparatus 100 has been described as an example of the endoscope system according to the embodiment of the present invention, the endoscope system according to the embodiment of the present invention may be realized by a plurality of devices connected to each other via the network. For example, a configuration may be adopted in which at least a part of the processing by the control device 4 described above is executed by another device connected to the endoscope apparatus 100 via the network.

(Another Embodiment of Display Unit)

Although the display device 7 has been described as an example of the display unit according to the embodiment of the present invention, the display unit according to the embodiment of the present invention may be realized by a plurality of display devices. In this case, the main region described above may be composed of one display device of the plurality of display devices, and the sub-region described above may be composed of the remaining display devices of the plurality of display devices.

(Control Program)

A control program, which is stored in the ROM of the control device 4, is stored in a program computer-readable non-transitory storage medium. Examples of such a "computer-readable storage medium" include an optical medium, such as a compact disc-ROM (CD-ROM), and a magnetic storage medium, such as a universal serial bus (USB) memory, or a memory card. In addition, such a program can also be provided by being downloaded via a network.

As described above, in the present specification, the following matters are disclosed.

(1)

An endoscope system comprising an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, in which the imaging unit performs imaging of the imaging target at a frame rate higher than a frame rate of display of the captured image displayed by the display unit, and the light source unit repeatedly performs an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

(2)

The endoscope system according to (1), in which a length of each of the first period and the second period is fixed in repetition of the operation or is variable in repetition of the operation.

(3)

The endoscope system according to (1) or (2), in which the spectrum of the illumination light emitted by the light source unit in the first period and the second period is fixed in repetition of the operation or is variable in repetition of the operation.

(4)

The endoscope system according to any one of (1) to (3), in which a non-irradiation period of the light source unit is present between the first period and the second period.

(5)

The endoscope system according to any one of (1) to (4), in which the imaging unit performs an imaging operation of a rolling shutter system, the second period is a period over a plurality of consecutive frames in imaging by the imaging unit, and the imaging control unit acquires at least information excluding captured image information for one frame in imaging by the imaging unit as captured image information of the second period for the captured image information immediately after start of the second period.

(6)

The endoscope system according to any one of (1) to (4), in which the imaging unit performs an imaging operation of a rolling shutter system, and the imaging control unit performs global reset of the imaging unit after the first period and acquires captured image information after the global reset is performed as captured image information of the second period.

(7)

The endoscope system according to any one of (1) to (4), in which the imaging unit performs an imaging operation of a global shutter system.

(8)

The endoscope system according to any one of (1) to (7), further comprising an analysis unit that performs analysis based on captured image information obtained by imaging of the second period in the captured image information, in which the display unit displays the captured image based on captured image information obtained by imaging of the first period in the captured image information.

(9)

The endoscope system according to (8), in which the display unit displays a screen including the captured image and a result of the analysis.

(10)

The endoscope system according to (8) or (9), in which the analysis includes analysis of an insertion shape of the endoscope.

(11)

The endoscope system according to any one of (8) to (10), in which the analysis includes extraction of a contour of the captured image based on the captured image information.

(12)

The endoscope system according to any one of (8) to (11), in which the analysis includes detection of a region-of-interest inside a subject into which the endoscope is inserted.

(13)

The endoscope system according to any one of (8) to (12), in which the analysis includes selection of a similar case image.

(14)

The endoscope system according to any one of (8) to (13), in which the analysis includes determination of a tumor and a non-tumor.

(15)

The endoscope system according to any one of (8) to (14), in which the analysis includes specifying of a state of an organ.

(16)

The endoscope system according to any one of (8) to (15), in which the analysis includes generation of a planned separation line.

(17)

The endoscope system according to any one of (1) to (16), in which the first period is a period longer than the second period.

(18)

The endoscope system according to any one of (1) to (17), in which the illumination light emitted by the light source unit in the first period and the second period is white light or light for image-enhanced endoscopy.

(19)

A control method of an endoscope system including an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, the method comprising performing, by the imaging unit, imaging of the imaging target at a frame rate higher than a frame rate of display of the captured image displayed by the display unit, and repeatedly performing, by the light source unit, an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

(20)

A non-transitory computer readable recording medium storing a control program controlling an endoscope system including an endoscope including an imaging unit, a light source unit that irradiates an imaging target, imaged by the imaging unit, with illumination light, an imaging control unit that generates captured image information based on an imaging signal obtained from the imaging unit, and a display unit that displays a captured image based on the captured image information, the program causing a computer to execute a process comprising causing the imaging unit to perform imaging of the imaging target at a frame rate higher than a frame rate of display of the captured image displayed by the display unit, and causing the light source unit to repeatedly perform an operation of continuously emitting the illumination light in a first period over a plurality of consecutive frames in imaging by the imaging unit, and then emitting illumination light having a spectrum different from a spectrum of the illumination light emitted in the first period in a second period which is a period over at least one frame in imaging by the imaging unit.

From the above description, the imaging apparatus according to the following supplementary note 1 can be grasped.

[Supplementary Note 1]

An endoscope system comprising an endoscope including an imaging sensor, a light source device that irradiates an imaging target, imaged by the imaging sensor, with illumination light, an imaging control processor that generates captured image information based on an imaging signal obtained from the imaging sensor, and a display device that displays a captured image based on the captured image information, in which the imaging sensor performs imaging of the imaging target at a frame rate higher than a frame rate of display of the captured image displayed by the display device, and the light source device repeatedly performs an operation of continuously emitting the illumination light in a first period over a plurality of consecutive frames in imaging by the imaging sensor, and then emitting illumination light having a spectrum different from a spectrum of the illumination light emitted in the first period in a second period which is a period over at least one frame in imaging by the imaging sensor.

According to the present invention, it is possible to provide the endoscope system, the control method, and the non-transitory computer readable recording medium storing a control program that can display the high-quality live image based on imaging with the normal light while also performing imaging with the special light.

EXPLANATION OF REFERENCES

1: endoscope
4: control device
5: light source device
6: input unit
7: display device
10: insertion part
10A: flexible part
10B: bendable part
10C: distal end part
11: operating part 12: angle knob
13: universal cord
13A, 13B: connector portion
21: objective lens
22: lens group
23: imaging element
25: memory
26, 41: communication I/F
27: imaging driving unit
42: signal processing unit
42a: captured image information generation unit
42b: live image generation unit
42c: analysis unit
42d: analysis image generation unit
43: display controller
44: system control unit
45: recording medium
50: illumination lens
51: light source processor
52: light source unit
52a: V-LED
52b: B-LED
52c: G-LED
52d: R-LED
53: light guide
54: optical path coupling unit
60: imaging surface
61: pixel
62: pixel row
63: drive circuit
64: signal processing circuit
70: screen
71: main screen
72: sub-screen
81: illumination light timing
82: imaging timing
82a, 82b, 82c, 82d, 82e: imaging
83: main screen display timing
83a: main screen display
84: sub-screen display timing
84b, 84c: sub-screen display
91: global reset
100: endoscope apparatus

What is claimed is:

1. An endoscope system comprising:
an endoscope including an imaging sensor;
a light source device that irradiates an imaging target, imaged by the imaging sensor, with white light and special light having a spectrum different from a spectrum of the white light;
a processor that generates captured image information based on an imaging signal obtained from the imaging sensor; and
a display device that displays a captured image based on the captured image information, the display device including a first area and a second area, the second area being a single display area that is different from the first area and smaller than the first area,
wherein the processor is configured to:
control the light source device such that the light source device repeatedly performs an operation in which the light source device emits the white light in a first period spanning a plurality of consecutive frames, and the light source device emits the special light in a second period spanning at least one frame;
acquire a plurality of white light images imaged, for the first period, at a first imaging frame rate;
acquire a plurality of special light images imaged, for the second period, at a second imaging frame rate;
subsequently display the plurality of white light images on the first area; and
subsequently display the plurality of special light images on the second area,
the first imaging frame rate is higher than a display frame rate of display of image displayed by the display device, and
the second imaging frame rate is less than the display frame rate.

2. The endoscope system according to claim 1,
wherein a length of each of the first period and the second period is fixed in repetition of the operation or is variable in repetition of the operation.

3. The endoscope system according to claim 1,
wherein the spectrum of the white light emitted by the light source device in the first period and the spectrum of the special light emitted by the light source device in the second period are fixed in repetition of the operation or are variable in repetition of the operation.

4. The endoscope system according to claim 1,
wherein the imaging sensor performs an imaging operation of a rolling shutter system,
the second period is a period over a plurality of consecutive frames in imaging by the imaging sensor, and
the processor acquires at least information excluding captured image information for one frame in imaging by the imaging sensor as captured image information of the second period for the captured image information immediately after start of the second period.

5. The endoscope system according to claim 1,
wherein the imaging sensor performs an imaging operation of a rolling shutter system, and
the processor performs a global reset of the imaging sensor after the first period and acquires captured image information after the global reset is performed as captured image information of the second period.

6. The endoscope system according to claim 1,
wherein the imaging sensor performs an imaging operation of a global shutter system.

7. The endoscope system according to claim 1,
wherein the processor performs analysis based on captured image information obtained by imaging of the second period in the captured image information,
wherein the display device displays the captured image based on captured image information obtained by imaging of the first period in the captured image information.

8. The endoscope system according to claim 7,
wherein the display device displays a screen including the captured image and a result of the analysis.

9. The endoscope system according to claim 7,
wherein the analysis includes analysis of an insertion shape of the endoscope.

10. The endoscope system according to claim 7,
wherein the analysis includes extraction of a contour of the captured image based on the captured image information.

11. The endoscope system according to claim 7,
wherein the analysis includes detection of a region-of-interest inside a subject into which the endoscope is inserted.

12. The endoscope system according to claim 7,
wherein the analysis includes selection of a similar case image.

13. The endoscope system according to claim 7,
wherein the analysis includes determination of a tumor and a non-tumor.

14. The endoscope system according to claim 7,
wherein the analysis includes specifying of a state of an organ.

15. The endoscope system according to claim 7,
wherein the analysis includes generation of a planned separation line.

16. The endoscope system according to claim 1,
wherein the first period is a period longer than the second period.

17. A control method of an endoscope system including an endoscope including an imaging sensor, a light source device that irradiates an imaging target, imaged by the imaging sensor, with white light and special light having a spectrum different from a spectrum of the white light, a processor that generates captured image information based on an imaging signal obtained from the imaging sensor, and a display device that displays a captured image based on the captured image information, the display device including a first area and a second area, the second area being a single display area that is different from the first area and smaller than the first area, the method comprising:
   controlling the light source device such that the light source device repeatedly performs an operation in which the light source device emits the white light in a first period spanning a plurality of consecutive frames, and the light source device emits the special light in a second period spanning at least one frame;
   acquiring a plurality of white light images imaged, for the first period, at a first imaging frame rate;
   acquiring a plurality of special light images imaged, for the second period, at a second imaging frame rate;
   subsequently displaying the plurality of white light images on the first area; and
   subsequently displaying the plurality of special light images on the second area,
   wherein the first imaging frame rate is higher than a display frame rate of display of image displayed by the display device, and
   the second imaging frame rate is less than the display frame rate.

18. A non-transitory computer readable recording medium storing a control program controlling an endoscope system including an endoscope including an imaging sensor, a light source device that irradiates an imaging target, imaged by the imaging sensor, with white light and special light having a spectrum different from a spectrum of the white light, a processor that generates captured image information based on an imaging signal obtained by the imaging sensor, and a display device that displays a captured image based on the captured image information, the display device including a first area and a second area, the second area being a single display area that is different from the first area and smaller than the first area, the program causing a computer to execute a process comprising:
   controlling the light source device such that the light source device repeatedly performs an operation in which the light source device emits the white light in a first period spanning a plurality of consecutive frames, and the light source device emits the special light in a second period spanning at least one frame;
   acquiring a plurality of white light images imaged, for the first period, at a first imaging frame rate;
   acquiring a plurality of special light images imaged, for the second period, at a second imaging frame rate;
   subsequently displaying the plurality of white light images on the first area; and
   subsequently displaying the plurality of special light images on the second area,
   wherein the first imaging frame rate is higher than a display frame rate of display of image displayed by the display device, and
   the second imaging frame rate is less than the display frame rate.

* * * * *